(12) United States Patent
Gleich et al.

(10) Patent No.: US 7,619,408 B2
(45) Date of Patent: Nov. 17, 2009

(54) SPATIALLY RESOLVED DETERMINATION OF MAGNETIC PARTICLE ANISOTROPY IN AN AREA OF EXAMINATION

(75) Inventors: Bernhard Gleich, Hamburg (DE); Jürgen Weizenecker, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 461 days.

(21) Appl. No.: 10/552,809

(22) PCT Filed: Apr. 15, 2004

(86) PCT No.: PCT/IB2004/050446

§ 371 (c)(1), (2), (4) Date: Oct. 11, 2005

(87) PCT Pub. No.: WO2004/091395

PCT Pub. Date: Oct. 28, 2004

(65) Prior Publication Data

US 2006/0211938 A1   Sep. 21, 2006

(30) Foreign Application Priority Data

Apr. 15, 2003   (EP)   .................................. 03101018

(51) Int. Cl.
*G01N 27/72* (2006.01)
*G01R 33/12* (2006.01)
(52) U.S. Cl. ........................ 324/228; 324/240; 324/204; 324/226
(58) Field of Classification Search ................. 324/201, 324/204, 228, 214, 226, 239–244, 260
See application file for complete search history.

(56) References Cited

U.S. PATENT DOCUMENTS

| 6,470,220 B1 * | 10/2002 | Kraus et al. | .................. 607/103 |
| 6,927,570 B2 * | 8/2005 | Simmonds et al. | .......... 324/239 |
| 2003/0085703 A1 * | 5/2003 | Gleich | ........................ 324/309 |

FOREIGN PATENT DOCUMENTS

| DE | 37 51 918 T2 | 6/1987 |
| DE | 3751918 T2 | 3/1997 |

(Continued)

OTHER PUBLICATIONS

Hinshaw, "Image Formation by Nuclear Magnetic Resonance: The Sensitive-Point Method", Appl. Phys. 47, 1976, pp. 3709-3721.
Damadian et al, "Tumor Imaging in a Live Animal by Field Focusing NMR (Fonar)", Physiol. Chem. Phys. 8, 1976, pp. 61-65.

*Primary Examiner*—Jay M Patidar

(57) ABSTRACT

Determination of at least one of physical, chemical and biological properties and parameters within an area of examination of an object of examination by introducing magnetic particles in at least a portion of the area of examination, generating a magnetic field with a spatial distribution of the magnetic field strength such that the area of examination includes a first sub-area with lower magnetic field strength and a second sub-area with a higher magnetic field strength, changing the spatial location of both sub-areas in the area of examination so that the magnetization of the particles changes locally, acquiring signals that depend on the magnetization in the area of examination influenced by the changing of the spatial location of both sub-areas, and evaluating the signals to obtain information about the anisotropy of the magnetic particles in the area of examination.

21 Claims, 1 Drawing Sheet

FOREIGN PATENT DOCUMENTS

Figure 1:
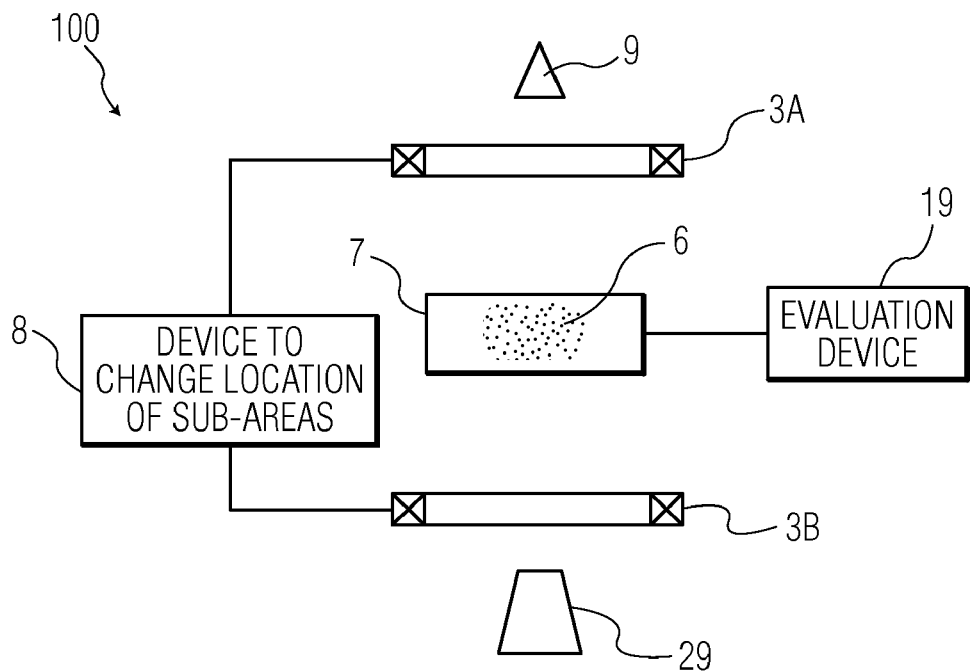

| | | | |
|---|---|---|---|
| DE | 10151778 A1 | 8/2003 |
| EP | 0 095 124 A1 | 11/1983 |
| EP | 0095124 A1 | 11/1983 |
| EP | 1304542 A2 | 4/2003 |

* cited by examiner

SPATIALLY RESOLVED DETERMINATION OF MAGNETIC PARTICLE ANISOTROPY IN AN AREA OF EXAMINATION

The present invention relates to a method for the spatially resolved determination of, particularly, physical, chemical and or/biological properties or parameters and/or the changes in, particularly, physical, chemical and or/biological properties or parameters within the area of examination in an object of examination. The invention further also relates to magnetic particle compositions having improved magnetic imaging properties for use in the method according to the invention. The present invention also relates to a method and an apparatus having improved spatial resolution in the method according to the invention.

The expert has numerous direct and indirect measurement methods available to determine physical, chemical and biological parameters of every type depending on the task and the object under examination. Of particular interest are frequently those measurement methods with which condition parameters can be determined in media that are not immediately accessible by a measurement device or measurement sensor. Suitable examples for indirect parameter determination are the tracking of reaction parameters such as temperature and reaction progress in chemical production processes using optical methods or the evaluation of tool component quality, for example, the existence of cracks using ultrasound. Indirect measurement methods are often necessary in the investigation of living tissue for the determination of, for example, temperature, pH value or the concentration of specific constituents. Such indirect measurement methods are however regularly more complex and subject to greater measurement errors than direct determination methods. Increasing efforts are being made to find options of determining the parameters under examination very precisely, non-destructively and in an indirect manner for many production processes or products. Of particular value here are those measurement methods with which information can be specifically determined from local, tightly restricted areas in an object of examination.

A method for non-invasive determination of chemical and physical states inside an animal or human body is for instance described in EP 0 95 124 A. Here, using magnetic resonance spectroscopy with a homogenous constant magnetic field and a high frequency magnetic field, the temperature and pH values inside selected volume segments in an area of examination could be determined or specified from the parameters of a measured nuclear magnetic resonance spectrum.

In an embodiment of the method in EP 0 95 124 A, three orthogonally orientated gradient fields, asynchronously modulated, were generated in addition to the homogenous constant magnetic field, where a local magnetic resonance signal was recorded only at the interface between the three levels of the gradient fields. This embodiment is described in the literature as the "Sensitive point" method (see also Hinshaw, J. Appl. Phys. 47 (1976), pages 3709 to 3721). In addition, it is possible according to EP 0 95 124 A, to obtain statements about the temperature and pH value in living objects by superimposing a homogenous magnetic field over a gradient field in such a manner that only a restricted limited volume in the area of the measurement point being examined has a high homogeneity and all surrounding areas have a considerable inhomogeneity. This method is described in the literature as the "FONAR" method (see also Damadian, Physiol. Chem. Phys. 8 (1976), pages 61 to 65). The disadvantage in the EP 0 95 124 A measurement method is that it is not possible to shift or move the locally restricted area of examination in order to, e.g. obtain reliable statements over a larger, coherent area of examination or to follow local changes in the object of examination over time.

DE 37 51 918 T2 describes a method to obtain in-vivo images of an animal or human organ or tissue with the aid of nuclear magnetic resonance technology, in which an image-improving dose of nuclear magnetic resonance contrast agent, in the form of a superparamagnetic fluid, prepared in a specific manner, is used. The magnetic contrast agent influences the magnetic properties of the tissue under examination so that the irradiated protons show improved relaxation behavior. Superparamagnetic and ferromagnetic substances make the magnetic resonance image appear darker due to the reduction of $T_2$. However, suitable contrast agents for magnetic resonance imaging require extremely stable solutions to effectively increase the sensitivity of magnetic resonance measurement. The stability of suitable aqueous fluids of superparamagnetic iron oxides is however frequently limited considerably by clumping caused by magnetic forces of attraction between particles. DE 37 51 918 T2 proposes a four stage method for the production of a stable superparamagnetic fluid comprising bivalent and trivalent metal salts. This method is very time and cost intensive and is therefore not necessarily suitable for standard examinations. In addition, nuclear spin tomography requires the use of very strong magnetic fields with high homogeneity. In general, superconducting coils are used together with liquid helium cooling.

Figure 2:
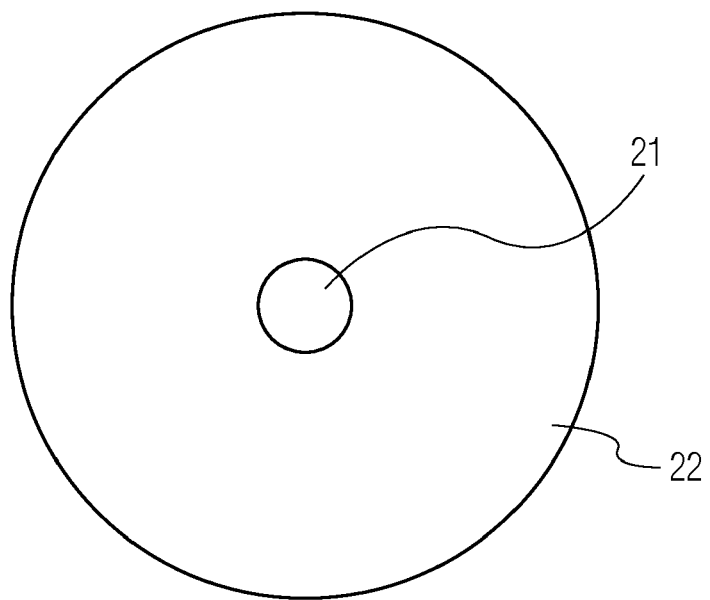

The present system will be described in detail hereinafter, by way of example, with reference to drawings, wherein:

FIG. 1 shows an apparatus for carrying out the method in accordance with the present system, and FIG. 2 shows magnetic field sub-areas produced by a coil provided in accordance with the present system.

A description of the present system will be provided with reference to FIG. 1 which shows an apparatus for carrying out the method in accordance with the present system, and FIG. 2 which shows magnetic field sub-areas produced by a coil provided in accordance with the present system. In FIG. 1, an arrangement 100 is shown for carrying out the method according to the present system. The arrangement includes at least one device 3a, 3b for generating a magnetic gradient field in at least one examination area of an examination object. The device 3a, 3b is operable to generate a magnetic field with a spatial profile of the magnetic field strength such as shown in FIG. 2. As shown, there is produced in the examination area, a first sub-area 21 having a low magnetic field strength and a second sub-area 22 having a higher magnetic field strength. A device 8 is provided to change the spatial location of both sub-areas 21, 22 in the area of examination so that a magnetization of particles 6 changes locally. A high frequency generating device 9 is provided to generate a high frequency field to irradiate the area of examination such that the temperature of the magnetic particle spin system is increased. A coil 7 is provided to acquire signals that depend on the magnetization in the area of examination influenced by this change. An evaluation device 19 is coupled to the coil 7 for evaluating the signals to obtain information about the spatial distribution of the signals in the area of information. The area of examination may be subject to sound by a sound producing device 29 that causes magnetostriction in at least a portion of the magnetic particles.

The object of the present invention was to make accessible a method to determine, in particular local parameters in an area of examination using simpler, therefore more-cost effective equipment, in a reproducible and precise manner, without the disadvantages inherent in the state of the art measurement methods and which provides an improved spatial resolution.

Another object of the present invention was to provide a method for the local determination of physical, chemical or biological parameters or parameter changes that can be used for in-situ determination of these parameters and therefore permit the examination of materials and of living material.

A method was therefore developed for the spatially resolved determination of, particularly, physical, chemical and/or biological properties or parameters and/or changes in, particularly, physical, chemical and/or biological properties or parameters within the area of examination of an object of examination by determining the changes in spatial resolution, concentration and/or anisotropy of the magnetic particles in this area of examination or in portions thereof in dependence on the effect of, particularly, physical, chemical and/or biological influencing variables on at least a partial area, and/or the, particularly, physical, chemical and/or biological conditions in at least a partial area of the area of examination by means of the following steps:

a) Introduction of magnetic particles in at least a portion of the area of examination in a condition that is irreversible or reversible, particularly periodically, modifiable or modified by, particularly, physical, chemical and/or biological influencing variables that affect the area of examination or by conditions at the area of examination,
b) Generation of a magnetic field with a spatial distribution of the magnetic field strength such that the area of examination consists of a first sub-area with lower magnetic field strength and a second sub-area with a higher magnetic field strength,
c) Change of the spatial location of both sub-areas in the area of examination so that the magnetization of the particles changes locally,
d) Acquisition of signals that depend on the magnetization in the area of examination influenced by this change, and
e) Evaluation of said signals to obtain information about the spatial distribution, concentration and/or permanent or temporary anisotropy of the magnetic particles or the changes in these parameters in the area of examination.

The present method more particularly uses the fact that the magnetic response signal changes dependent on the concentration, type, distribution and magnetic anisotropy in the area of examination. Anisotropy means both a form or crystal anisotropy and an effective anisotropy. Effective anisotropy means the anisotropy resulting from the form anisotropy and the average crystal anisotropy.

One embodiment of the present method according to the invention provides that the respective conditions or parameters and/or external influencing variables are detected in an area of examination where the distribution and/or anisotropy of the magnetic particles changes or is changed in at least one portion of the area of examination.

It has been shown to be particularly advantageous when the magnetic particles, as per the condition in step a) generally have a uniform form, especially a round form and/or such a form that the magnetic particles have no preferential direction from a magnetic aspect. Such magnetic particles generate, when distributed in an area of examination, a characteristic magnetization characteristic curve in the gradient field in the method according to the invention. If the aforesaid described form is released, a modified magnetization characteristic curve results. This deviation from a form without preferential direction can be detected with high sensitivity with the method according to the invention.

One embodiment of the method according to the invention provides that the magnetic particles are enzymatically broken down or metabolized in the area of examination. It is known that magnetic particles based on iron oxides, used e.g. as contrast agents in nuclear spin tomography, are metabolized or broken down by enzymes in the organism. There have been many attempts to hinder this degradation, e.g. by suitable coatings, in order to obtain longer measurement periods. The magnetic particles used are mainly utilized, locally restricted, to examine the metabolism. The method according to the invention ensures sensitivity sufficient to track changes in the anisotropy of the magnetic particles caused by the metabolisation of the particles in the examination area. In particular, it is possible to distinguish in the imaging technique between the areas having a high metabolic activity and the area as having a low metabolic activity. This difference can be used to identify for example different regions inside the human body. It is advantageous to administer particles at the start of the examination that have a uniform level of anisotropy and use the spatially resolved degeneration of the uniformity to develop an image of biological activity in the examination area.

In another embodiment of the method according to the invention, the area of examination can be subject to sound that causes magnetostriction in at least a portion of the magnetic particles. Magnetostriction causes the magnetic particles, when subjected to a suitable sound, to stretch and shear causing a temporary change in crystal anisotropy. This can also be used to significantly improve the spatial resolution when imaging the area of examination. Also the sound field or any applied static or dynamic stress in the object may be measured using the change in anisotropy.

The spatial resolution during imaging of the area of examination can therefore be significantly improved so much that the permanent or temporary change in anisotropy, especially the effective anisotropy, can be detected.

The invention also provides that the changes in spatial distribution and/or the permanent or temporary anisotropy of the magnetic particles detected in the area of examination can be correlated with a local concentration, temperature, sound level and/or a local pH value and/or the presence or absence of one or more enzymes. For example, the anisotropy of a magnetic particle changes when it is fully or partially destroyed or metabolized by external influences.

Another embodiment of the present invention proposes a method to improve the resolution during determination of the spatial distribution of magnetic particles in an area of examination, comprising the following steps:

a) Generation of a magnetic field with a spatial distribution of the magnetic field strength such that the area of examination consists of a first sub-area with lower magnetic field strength and a second sub-area with a higher magnetic field strength,
b) Change of the spatial location of both sub-areas in the area of examination so that the magnetization of the particles changes locally,
c) Acquisition of signals that depend on the magnetization in the area of examination influenced by this change, and
d) Evaluation of said signals to obtain information about the spatial distribution of the signals in the area of examination, where a high frequency field is irradiated in the area of examination so that the temperature of the magnetic particle spin system is increased.

A high frequency field with a frequency in the range between circa 100 kHz to circa 100 GHz, preferably from circa 10 MHz to circa 200 MHz, has been found to be particularly effective. Therefore high frequency fields in the sense of the present invention also comprise frequencies in the range from 10 to 100 MHz. It is preferred that the frequency of the high frequency field is higher than the frequency of scanning in the examination area. The increase of the temperature of the magnetic particle spin system results in a better resolution and gives access to particles that could not adequately respond to the external magnetic field. This method is especially suitable when the magnetic particles used are not fully round and/or have a form that shows a preferential magnetic direction. The method may be also used to measure the spatial distribution of the RF field in the object.

The invention further also relates to an arrangement for carrying out the method according to the invention, comprising at least one device for generating a magnetic gradient field in at least one examination area of an examination object (A), said device comprising a means for generating a magnetic field with a spatial profile of the magnetic field strength such that there is produced in the examination area a first sub-area having a low magnetic field strength and a second sub-area having a higher magnetic field strength, means to change the spatial location of both sub-areas in the area of examination so that the magnetization of the particles changes locally, high frequency generating means to generate a high frequency field to irradiate the area of examination such that the temperature of the magnetic particle spin system is increased, means to acquire signals that depend on the magnetization in the area of examination influenced by this change and evaluation means for evaluating said signals to obtain information about the spatial distribution of the signals in the area of information. The high frequency generating means preferably can generate a frequency between 100 kHz and 100 GHz, preferably 10 to 100 MHz.

The method according to the invention makes considerable use of an arrangement described in the unpublished German patent application, file number 101 51 778.5. This refers also to the preferred embodiments of this arrangement in the above patent application.

The arrangement used in the invention generates a spatially inhomogenous magnetic field in the area of examination. In the first sub-area, the magnetic field is so weak that the magnetization of the particle deviates more or less strongly from the external field and is therefore not saturated. This first sub-area is preferentially a spatially coherent area; it can however also be a punctiform area, but also a line or a plane. In the second sub-area (i.e. the rest of the area of examination lying outside the first area), the magnetic field is sufficiently strong to hold the particle in a state of saturation. Magnetization is saturated when the magnetization has aligned almost all particles in approximately the direction of the external magnetic field so that with an increase in magnetic field, the magnetization in that area increases considerably less than in the first sub-area with a similar increase in magnetic field.

By changing the position of the two sub-areas within the area of examination, the (total) magnetization in the area of examination changes. If, therefore, the magnetization in the area of examination or the physical parameters influenced by this are measured, information can be derived about the spatial distribution of the magnetic particles in the area of examination.

To change the spatial position of both sub-areas in the area of examination or to change the magnetic field strength in the first sub-area, an e.g. magnetic field that is localized and/or changes over time can be generated. It is also provided that the signals induced in at least one coil by the change over time of the magnetization in the area of examination are acquired and evaluated to obtain information about the spatial distribution of magnetic particles in the area of examination. The biggest possible signals are achieved by changing the spatial position of both sub-areas as rapidly as possible. A coil, with which a magnetic field can be generated in the area of examination, can be used to acquire the signals. Preferably, at least one separate coil is used.

If the change in the spatial position of the sub-area is implemented, e.g. using a magnetic field changing over time, this can induce a similarly periodic signal in a coil. The acquisition of this signal may however be difficult as the signals generated in the area of examination and the magnetic field changing over time are simultaneously effective: it is therefore not possible to differentiate between the signals induced by the magnetic field and the signals induced by the change in magnetization in the area of examination. This can however be avoided in that a magnetic field changing over time acts on a first frequency band in the area of examination and that a second frequency band, which contains higher frequency components than the first frequency band, in the signal received from the coil is evaluated to obtain information about the spatial distribution of the magnetic particles. This exploits the fact that the frequency components of the second frequency band can only be created by a change in the magnetization in the area of examination due to the non-linearity of the magnetization characteristic curve. When the magnetic field changing over time has a sinusoidal periodic behavior, the first frequency band consists only of a single frequency component—the sinusoidal fundamental oscillation. In contrast, the second frequency band contains, in addition to this fundamental oscillation, higher harmonics (so-called harmonic waves) of the sinusoidal fundamental oscillation which can be used for evaluation.

A preferred arrangement for the method according to the present invention is characterized in that the means for generating the magnetic field includes a gradient coil arrangement for generating a magnetic gradient field which reverses its direction in the first sub-area of the area of examination and shows a zero passage. This magnetic field is—when the gradient coil arrangement, e.g. comprises two identical windings carrying opposing flows located on either side of the area of examination (Maxwell coil)—zero at a point on the winding axis and increases almost linearly on both sides of this point with opposite polarities. It is only with these particles located in the area around this field zero point where magnetization is not saturated. For particles outside this area, the magnetization is in a state of saturation.

Therefore an arrangement can be provided with means to generate a magnetic field changing over time and superimposed on the magnetic gradient field for the purpose of moving both sub-areas in the area of examination. The area generated by the gradient coil arrangement is therefore moved around the field zero point, i.e. the first sub-area, within the area of examination by the magnetic field changing over time. With appropriate changes over time and orientation of this magnetic field it is possible to move the field zero point throughout the entire area of examination.

The magnetization change resulting from the movement of the field zero point can be detected by an appropriate coil arrangement. The coil used to detect the signals generated in the area of examination can be a coil that is already used to generate the magnetic field in the area of examination. There are, however, advantages to using a separate coil for reception as this can be decoupled from the coil arrangement producing a magnetic field that changes over time. In addition, an improved signal/noise ratio can be achieved with a coil—and more so with several coils.

The amplitude of the signals induced in the coil arrangement increases the faster the position of the field zero point changes in the area of examination, i.e. the faster the magnetic field changing over time superimposed on the magnetic gradient field changes. It is however technically difficult to generate a magnetic field changing over time with sufficient amplitude to move the field zero point at the point of the area of examination or with sufficiently large change speed to generate signals with sufficient amplitude. Particularly suitable arrangements for this purpose comprise means to generate a first and at least a second magnetic field superimposed on the magnetic gradient field, where the first magnetic field moves slowly with high amplitude and the second magnetic field moves fast with low amplitude. This generates—preferably by two coil arrangements—two magnetic fields with different speeds and different amplitudes. Another advantage is that the field changes can be so fast (e.g. >20 kHz) that they lie above the human limit of audibility. It can also be provided that both magnetic fields in the area of examination are generally aligned vertically to one another. This enables the movement of the field-free point within a two-dimensional area. This can be expanded to a three-dimensional area by another magnetic field comprising a component aligned vertically to the two magnetic fields. Another advantage is inherent in an arrangement with a filter downstream of a coil arrangement which suppresses the signal components in a first frequency band in the signal induced by the coil arrangement and allows the signal components in a second frequency band, which contains higher frequency components than the first frequency components, to pass. This exploits the fact that the magnetization characteristic curve is non-linear in the area where the magnetization transitions from the non-saturated to the saturated state. This non-linearity has the effect that, e.g. a sinusoidal magnetic field over time with the frequency f generates, in the area of non-linearity, an induction changing over time with the frequency f (fundamental oscillation) and integer multiples of the frequency f (harmonic waves or higher harmonics). The evaluation of the higher harmonics has the advantage that the fundamental oscillation of the magnetic field used to move the field-free point does not have any influence on the evaluation.

According to the present invention, it is provided that the magnetic particles become saturated when an external magnetic field is applied, especially one with a strength of circa 100 mT or less. Of course, larger saturation field strengths are also suitable for the method according to the invention.

Suitable magnetic field strengths for many applications are already circa 10 mT or less. This strength would already be sufficient for many tissue or organ examinations. But it is also possible to achieve good measurement results with field strengths in the area of 1 mT or less, or circa 0.1 mT or less. For example, concentration data, temperature, pressure or pH values can be determined with high accuracy and resolution with magnetic fields of circa 10 mT or less, circa 1 mT or less and circa 0.1 mT or less.

In the sense of the present invention, an external magnetic field, where the magnetic particles become or are saturated, means a magnetic field where circa half the saturation magnetization is achieved.

Suitable magnetic particles here are those that can reach saturation with a sufficiently small magnetic field. A necessary requirement for this is that the magnetic particles have a minimum size or a minimum dipole moment. The term magnetic particle in the sense of the present invention also comprises particles that can be magnetized.

Suitable magnetic particles favorably have dimensions that are small compared to the size of the voxel whose magnetization is to be determined by the method according to the invention. In addition, the magnetization of the particles should preferably reach saturation at the lowest possible field strengths of the magnetic field. The lower the field strength required for this is, the higher the spatial resolution capacity or the weaker the (external) magnetic field being generated in the area of examination can be. In addition, the magnetic particles must have the highest possible dipole moment or a high saturation induction so that the change in magnetization produces the largest possible output signals. It is also important for the particles not to be toxic if the method is to be used for medical examinations.

A preferred form of the present method according to the invention proposes that the magnetic particle is a mono-domain particle that can be reverse magnetized by Neel rotation and/or that the reverse magnetization is caused by Brownian rotation.

Suitable magnetic mono-domain particles are preferably dimensioned so that only a single magnetic domain (the mono-domain) can be formed in them or Weiß areas are not present. Suitable particle sizes in a specially preferred embodiment of the present invention lie in the range between 20 nm to ca. 800 nm, where the upper limit is also dependent on the material used. Preferably, magnetite ($Fe_3O_4$), maghemite ($\gamma$-$Fe_2O_3$) and/or non-stoichiometric magnetic iron oxides are used as mono-domain particles.

In general it is advantageous, especially when a rapid reverse magnetization based on Neel rotation is required, that the mono-domain particles have a low effective anisotropy. Effective anisotropy means the anisotropy resulting from the form anisotropy and the average crystal anisotropy. In the above-mentioned case a change in magnetization direction does not require the particle to be turned.

Alternatively, mono-domain particles with high effective anisotropy can be used when it is desired that the reverse magnetization, when applying an external magnetic field, is implemented by Brownian or geometric rotation. Above all, particles whose reverse magnetization is based on Neel rotation and on Brownian rotation are particularly suitable for viscosity measurements.

An alternative embodiment of the present method according to the invention proposes that the magnetic particle may be represented by a hard or soft magnetic multi-domain particle. These multi-domain particles are usually larger magnetic particles in which a number of magnetic domains can be formed. Such multi-domain particles suitably have a low saturation induction.

Hard magnetic multi-domain particles generally have the same magnetic properties as mono-domain particles with higher effective anisotropy. Soft magnetic multi-domain particles with low saturation magnetization have the advantage that they can be shaped into any form for use in the present method according to the invention. If they have an asymmetrical external form, they are then particularly suitable for local viscosity measurements in the area of examination. Soft magnetic multi-domain particles with high saturation magnetization must preferably be designed so that the demagnetizing factor becomes small. Both symmetrical and asymmetrical forms can be considered here. For example, a soft magnetic material with high saturation magnetization can be applied as a thin coating on a ball or cube that is not magnetizable. Soft magnetic multi-domain particles with high saturation magnetization that have an asymmetrical form, e.g. in the form of flakes or needles, can also be used for viscosity measurements.

Therefore, mono-domain particles, where reverse magnetization occurs via Neel and Brownian rotation, are particularly suitable for local viscosity measurements in the area of examination as are soft magnetic multi-domain particles with small or large saturation magnetization that have an asymmetrical external form.

As described above, the magnetic particles also comprise such particles that consist of a non-magnetic core and a coating of a magnetic material. Therefore this comprises in general all magnetic particles that have a low effective anisotropy and those that have a high effective anisotropy. A high coercive force $H_c$ is necessary in semi-hard and, especially, hard magnets in order to bring the magnetization to zero. Suitably hard magnetic materials comprise Al—Ni, Al—Ni—Co and Fe—Co—V alloys as well as barium ferrite (BaO 6xFe20$_3$).

In general the magnetic particles in the magnetic particle administering composition, are chosen such that good magnetic particle images, in particular a good resolution can be obtained in a given field gradient. In unpublished German patent application number 101 51778.5 a magnetic particle imaging method is described. It is generally described that magnetic mono-domain particles having a size between 20 and 800 nanometres or a glass beat coated with a magnetic coating can be used in this method. However, in order to achieve a good magnetic imaging contrast and resolution at relatively low magnetic field gradients, improved magnetic particle compositions are highly desirable. The inventors have found magnetic particles having improved magnetic particle imaging properties.

Preferably, the magnetic particles in the magnetic particle administering composition have a magnetization curve having a step change, the step change being characterized in that the magnetization change, as measured in an aqueous suspension, in a first field strength window of magnitude delta around the inflection point of said step change is at least a factor 3 higher than the magnetization change in the field strength windows of magnitude delta below and/or in the field strength windows of magnitude delta above the first field strength window, wherein delta is less than 2000 microtesla, preferably less than 1000 microtesla, and wherein the time in which the magnetisation step change is completed in the first delta window is less than 0.01 seconds, preferably less than 0.005 sec, more preferably less than 0.001, most preferably less than 0.0005 seconds. It is preferred that this step change in the delta window is at least a factor of three higher than in the delta window above and below the first delta window. It has been found, that such magnetic particles are particularly suitable for magnetic particle imaging, in particular for obtaining a good resolution of the image. It is further preferred, that the magnetic particle composition has a magnetisation curve, wherein the step change is at least 10%, preferably at least 20%, more preferably at least 30% and most preferably at least 50% of the total magnetisation of the particle composition as measured at an external magnetisation field of 1 Tesla. It is further preferred, that the magnetization change in the first field strength window of magnitude delta around the inflection point of said step change is at least a factor 4, preferably at least a factor 5 higher than the magnetization change in the field strength windows of magnitude delta below and/or in the field strength windows of magnitude delta above the first field strength window.

The magnetic particle composition is particularly useful for use in a magnetic particle imaging technique. The particles show good spatial resolution at relatively low field strength gradients. Further, the magnetic particle composition allows for a relatively high scanning speed for examining a large examination area. For example, for application in medical magnetic particle imaging, where the step change occurs preferably at a delta value below 1000 microTesla, the particle composition has a resolution value better than between 0.1 and 10 mm at magnetic field strength gradients between 10 and 0.1 T/m. With the magnetic particle imaging technique using the magnetic particle compositions according to the invention extremely good resolution can be obtained, for example in a range from 0.1 to 10 micrometres in applications, where are very high magnetic field is gradients can be achieved, for example in microscopy. It is noted that strictly speaking, magnetic field strength is expressed in H (A/m). However, in the present application, when reference is made to magnetic field strength, B-fields are meant. A magnetic fields B of 2000 µT as described above corresponds to an H field of 2 mT/$\mu_0$=1.6 kA/m, that is the equivalent H field that would produce a B field of 2 mT in vacuum.

A method for measuring the magnetisation curve and the required step change is as follows. A sample of a magnetic particle composition is suspended in water, optionally with the help of a simple detergent. To prevent clumping and/or to deagglomerate the magnetic particles an ultrasound treatment possible can be used. The concentration of the magnetic particle composition is less than 0.01 gr core mass per liter of solvent. With core mass is meant the mass of the magnetic material in the magnetic particle composition. The suspension is brought into a fast magnetometer. (i.e. a device that measures the magnetization of the sample while an external field is applied). Suitable fast magnetometers are known to the expert. The magnetometer is equipped with means allowing to produce an external field at the sample position in at least two orthogonal directions simultaneously, i.e. to produce any magnetic field below a given maximum amplitude and a given maximum speed of change. The magnetisation is measured also in at least two orthogonal directions in the same plane.

First the saturation magnetisation is measured. For this, a magnetic field of about one Tesla is applied in one direction and the magnitude of magnetization is measured after at least 10 seconds. Then the measurement sequences for determining the step change starts. The sequence starts with choosing a field vector with an external field magnitude below 20 mT. This field is applied for at most 100 seconds. Then a second direction is chosen. This direction defines the scalar values of the field H and the magnetization M. The field is rapidly changed, preferably less than 1 millisecond, so that it lies now in –H direction with some magnitude below 20 mT. Then the field is changed from –H to +H e.g. in a linear way and the (now scalar i.e. projected) magnetization is recorded. The magnetization curve is recorded in less than 0.01 s but longer than 1 µs. Where the magnetisation curve shows a step change, a first window of size delta is positioned centrally on the inflection point of the magnetisation step change. Similarly, a window of size delta is positioned below and above the first window, and the required step change is evaluated by determining the change in magnetisation in each of the windows.

Whether or not a given magnetic particle composition has the required step change depends in a complicated way on many variables, for example of the size of the particles, the particle size distribution, the shape of the particles, the damping constant for Neel rotation, the type of magnetic material, the crystallinity and the stochiometry of the composition of the magnetic material. It has been found that it is particularly important that the particle size distribution of the particle composition is narrow. Preferably, the magnetic particle composition according to the invention has a narrow particle size distribution wherein at least 50 weight % of the particles have a particle size between plus or minus 50%, preferably 25%, more preferably 10% of the average particle size. Preferably, the amount of particles within the specified windows, is at least 70 wt %, preferably at least 80 wt %, and most preferably at least 90 wt %. Particularly good results are obtained with mono-domain particles have a low magnetic anisotropy with a field needed for inducing Neel rotation of substantially below 10 mT, preferably below 5 mT, more preferably below 2 mT. Preferably, the magnetic particles are mono-domain particles having an average particle size between 20 and 80 nanometres, more preferably between 25 and 70 nanometres, must preferably between 30 and 60 nanometres, wherein at least 50, preferably at least 60, more preferably at least 70 weight % of the particles have a particle size between the average particle size plus or minus 10 nanometre.

In an alternative embodiment of the magnetic particle composition according to the invention, the magnetic particle is a multi-domain particle having substantially a needle shape having a demagnetisation factor of less than 0.001. This magnetic particle composition is particularly useful in non-medical applications where the needles shape is not a disadvantage. In another alternative embodiment, the magnetic particle composition according to the invention comprises magnetic particles comprising a non-magnetic core covered with a magnetic coating material, wherein the thickness of the coating is between 5 and 80 nanometres and wherein the demagnetisation factor is less than 0.01 and a diameter below 300 µm. Also in these alternative embodiments it is advantageous to have a small particle size distribution as described above. The physical parameters of the magnetic particles in these embodiments are preferably chosen to meet the step change requirement as described above for achieving good imaging properties.

The magnetic particle composition according to the invention can be manufactured by first forming magnetic particles, for example by precipitation, for example by contacting a solution comprising ferrous and ferric ions with a solution comprising sodium hydroxide as described above. In principle, a known precipitation process can be used. It is also possible to grind the particles from bulk material, for example using a high speed ball mill. The essential next step for obtaining a good magnetic particle composition is the selection and separation of the particles. The first step is to perform a size selection process by filtering and/or centrifuge methods. The next step is to perform a selection process based on the magnetic properties of the particles, for example, using oscillating magnetic gradient fields.

In a preferred magnetic particle composition for imaging the viscosity in an area of the examination the magnetic particles are a magnetic particles have the required step change as described above and have an anisotropy causing geometric rotation. The geometric rotation of the particles causes a modulation of the magnetisation reversal of the magnetic particles which is dependent on the speed of rotation and hence on the viscosity of the surrounding Medium. In particular, the anisotropy is preferably such that the internal anisotropy field in the particles is at least 0.1 mT, preferably at least 0.5 mT. When measured on the magnetic particle composition, the anisotropy is such that the magnetic particle composition shows an opening in the hysteresis loop of the magnetisation curve of at least 0.1 mT, preferably at least 0.5 mT. This most preferred magnetic particle composition can be used to significantly improve the resolution of the magnetic particle imaging technique by increasing the spin temperature of the magnetic particle spin systems by irradiation with a high frequency field.

A further application of the invention is in measuring and imaging the temperature in the examination area. The above described magnetic particles, in particular a magnetic particle composition wherein magnetic particles have a Curie temperature in a temperature range of interests in the examination area are very suitable for that purpose. For application of the imaging technique in a living organism the Curie temperature is between 30 and 50° C. In a preferred embodiment of the magnetic particle composition the composition comprises at least two different parts therein the magnetic particles have a different Curie temperature. In this particle composition the temperature dependence of the magnetisation of the overall particle composition can be adjusted within the temperature range of interest. Very accurate temperature measurements can be performed in this way.

Another method for a measuring and imaging the temperature in the examination area uses a magnetic particle composition wherein the magnetic particles have an anisotropy that is temperature dependant in a temperature window of interests in the examination area. Similarly, also here this preferred that the magnetic particle composition comprises at least two different parts wherein the magnetic particles have a different temperature dependence of the anisotropy.

The invention also relates to the use of a magnetic particle composition according to the invention in a method for a magnetic particle imaging as described above. The main application area for the magnetic particle compositions is in medical diagnosis. However, the technique and the magnetic particle compositions according to the invention can also be applied in other non-medical applications, for example in technical applications for investigating materials, processes and installations. For example, the invention also relates to the use of magnetic particle composition according to the invention in a method for the determination of the changes in spatial distribution, concentration and/or anisotropy of the magnetic particles, in particular the measurement of the viscosity or changes in the viscosity, in material processing, for example to study the rheology and solidification of a polymer material or the curing of a resin.

The present invention is based on the surprising recognition that very precise data about an area of examination can be obtained by taking into account the magnetic properties of the magnetic particles for example the anisotropy of magnetic particles or their changes or the influence of the property change on the magnetization characteristic curve that is characteristic for the area of examination. In this manner, an improved resolution can be obtained during the determination of the spatial distribution of magnetic particles in the area of examination, where, e.g. enzymatic breakdown of a particle or a metabolization process can be tracked with high sensitivity. It has also surprisingly been found that the resolution can be significantly improved by increasing the spin temperature of the magnetic particle spin systems by irradiation with a high frequency field. This method is especially suitable when the magnetic particles used are not fully round and/or have a form that shows a preferential magnetic direction. In addition, an improved resolution can be obtained by magnetostriction which is due to the effect of sound on the magnetic particles used.

The characteristics of the invention described above and in the claims can be used both individually and in any combination for the implementation of the invention in its various embodiments.

The invention claimed is:

1. A method for the spatially resolved determination of magnetic particle distribution for the determination of at least one of physical, chemical and biological properties and parameters within an area of examination of an object of examination, the method comprising acts of:
   introducing magnetic particles in at least a portion of the area of examination;
   generating a magnetic field with a spatial distribution of a magnetic field strength such that the area of examination includes a first sub-area with lower magnetic field strength and a second sub-area with a higher magnetic field strength;

changing the spatial location of both sub-areas in the area of examination so that the magnetization of the particles changes locally;

acquiring signals that depend on the magnetization in the area of examination influenced by the changing of the spatial location of both sub-areas; and evaluating the signals to obtain information about the anisotropy of the magnetic particles in the area of examination.

2. The method as claimed in claim 1, comprising an act of introducing an additional influencing variable including one of a high frequency field and a sound transmission in addition to the magnetic field into the area of examination where the at least one of a distribution and anisotropy of the magnetic particles is changed as a result of the introduced additional influencing variable in at least one portion of the area of examination.

3. The method as claimed in claim 1, wherein the magnetic particles have a form that the magnetic particles do not have a preferential magnetic direction.

4. The method as claimed in claim 1, comprising an act of selecting the magnetic particles to be one of enzymatically broken down or metabolized in at least one portion of the area of examination.

5. The method as claimed in claim 1, comprising an act of subjecting the area of examination to sound so that magnetostriction occurs in at least a portion of the magnetic particles.

6. The method as claimed in claim 1, wherein the act of evaluating the signals comprises an act of detecting a change in the anisotropy of the magnetic particle.

7. The method as claimed in claim 6, comprising an act of correlating the change anisotropy of the magnetic particles with at least one of a temperature, sound level and a local pH value.

8. The method as claimed in claim 6, comprising an act of correlating the change anisotropy of the magnetic particles with a presence or absence of one or more enzymes.

9. The method as claimed in claim 1, comprising an act of selecting a magnetic particle composition having a magnetization curve with a magnetization step change.

10. The method as claimed in claim 9, wherein the magnetization step change, as measured in an aqueous suspension, comprises a first field strength window of magnitude delta around an inflection point of the step change of at least a factor 3 higher than a magnetization change in field strength window of magnitude delta below the first field strength window, wherein delta is less than 2000 microtesla and wherein the time in which the magnetization step change is completed in the first field strength window is less than 0.01 seconds.

11. The method as claimed in claim 9, wherein the magnetization step change, as measured in an aqueous suspension, comprises a first field strength window of magnitude delta around an inflection point of the step change of at least a factor 3 higher than a magnetization change in field strength window of magnitude delta above the first field strength window, wherein delta is less than 2000 microtesla and wherein the time in which the magnetization step change is completed in the first field strength window is less than 0.01 seconds.

12. A method to improve resolution during a determination of a spatial distribution of magnetic particles in an area of examination, the method comprising acts of:

generating a magnetic field with a spatial distribution of the magnetic field strength such that the area of examination includes a first sub-area with lower magnetic field strength and a second sub-area with a higher magnetic field strength;

changing the spatial location of both sub-areas in the area of examination so that the magnetization of the particles changes locally;

introducing a high frequency field in the area of examination so that a temperature of a magnetic particle spin system is increased;

acquiring signals that depend on the magnetization in the area of examination influenced by the changing of the spatial location of both sub-areas; and evaluating the signals to obtain information about a spatial distribution of the signals in the area of examination.

13. The method as claimed in claim 12, wherein the high frequency field is introduced with a frequency in a range between 100 kHz to 100 GHz.

14. The method as claimed in claim 12, wherein the magnetic particles are mono-domain particles that are reverse magnetized by one of Neel rotation and Brownian rotation.

15. The method as claimed in claim 12, wherein the magnetic particles are hard magnetic multi-domain particles.

16. The method as claimed in claim 12, wherein the magnetic particles are soft magnetic multi-domain particles.

17. The method as claimed in claim 12, wherein the magnetic particles comprise hard magnetic materials.

18. The method as claimed in claim 17, wherein the hard magnetic materials comprise at least one of Al—Ni, Al—Ni—Co, Fe—Co—V alloys, and barium ferrite (BaO 6xFe$_2$O$_3$).

19. A device for improving resolution during a determination of a spatial distribution of magnetic particles in an area of examination, the device comprising:

a means for generating a magnetic field with a spatial distribution of the magnetic field strength such that the area of examination includes a first sub-area with lower magnetic field strength and a second sub-area with a higher magnetic field strength;

a means for changing the spatial location of both sub-areas in the area of examination so that the magnetization of the particles changes locally;

a high frequency generating means for generating a high frequency field to irradiate the area of examination such that the temperature of the magnetic particle spin system is increased;

a means for acquiring signals that depend on magnetization in the area of examination influenced by the changing of the spatial location of both sub-areas; and a means for evaluating the signals to obtain information about the spatial distribution of the signals in the area of examination.

20. The device according to claim 19, wherein the frequency generated by the high frequency generating means is between 100 kHz and 100 GHz.

21. The device according to claim 19, wherein the frequency generated by the high frequency generating means is between 10 and 100 MHz.

* * * * *